United States Patent
Brown

(10) Patent No.: US 7,490,609 B2
(45) Date of Patent: Feb. 17, 2009

(54) DENTAL APPLIANCE FOR MINIMIZING EFFECTS OF BRUXISM

(76) Inventor: Thomas W. Brown, 5811 Widmer, Shawnee, KS (US) 66216

( * ) Notice: Subject to any disclaimer, the term of this patent is extended or adjusted under 35 U.S.C. 154(b) by 286 days.

(21) Appl. No.: 10/986,492

(22) Filed: Nov. 10, 2004

(65) Prior Publication Data

US 2006/0096602 A1    May 11, 2006

(51) Int. Cl.
- *A61F 5/56* (2006.01)
- *A61C 5/14* (2006.01)
- *A61C 9/00* (2006.01)

(52) U.S. Cl. ............... 128/848; 128/859; 128/861; 128/862; 433/36

(58) Field of Classification Search ............ 128/859, 128/861, 862; 433/36
See application file for complete search history.

(56) References Cited

U.S. PATENT DOCUMENTS

| | | | |
|---|---|---|---|
| 3,532,091 A | 10/1970 | Lerman | |
| 4,115,893 A * | 9/1978 | Nakata et al. | 15/110 |
| 5,447,168 A | 9/1995 | Bancroft | |
| 5,873,365 A | 2/1999 | Brown | |
| 6,152,138 A | 11/2000 | Brown | |
| 6,164,278 A * | 12/2000 | Nissani | 128/848 |
| 6,978,786 B2 * | 12/2005 | Sabbagh | 128/859 |
| 2006/0011204 A1 * | 1/2006 | Maher | 128/861 |

* cited by examiner

*Primary Examiner*—P Bianco
*Assistant Examiner*—Tarla Patel
(74) *Attorney, Agent, or Firm*—Spencer Fane Britt & Browne LLP

(57) ABSTRACT

A dental appliance for maintaining a separation between the occlusal plane surfaces of the posterior teeth in order to avoid or minimize the adverse effects of bruxism, especially while sleeping. The appliance comprises bitepad assemblies, side assemblies for adjustably receiving the bitepad assemblies, and a strap assembly for connecting the side assemblies. Bitepad cores are provided with solid projections and mechanical locks that enhance bonding with associated overmolds for improved durability. Side assembly flanges are divided to achieve independent flexibility and improved conformity for enhanced stability and comfort. A mesial area of the connecting strap assembly is thickened and rigidified to create a flare in the areas of the cuspid roots to minimize irritation and discomfort to the gum tissue.

15 Claims, 3 Drawing Sheets

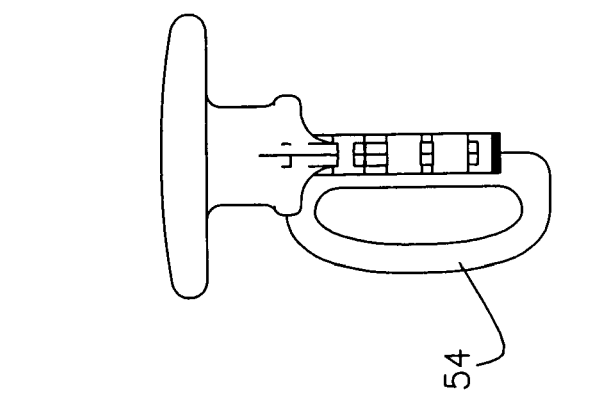
FIG. 7
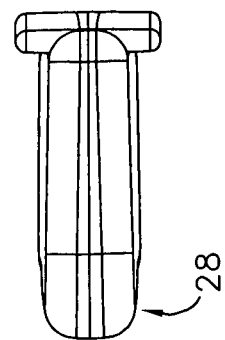
FIG. 6
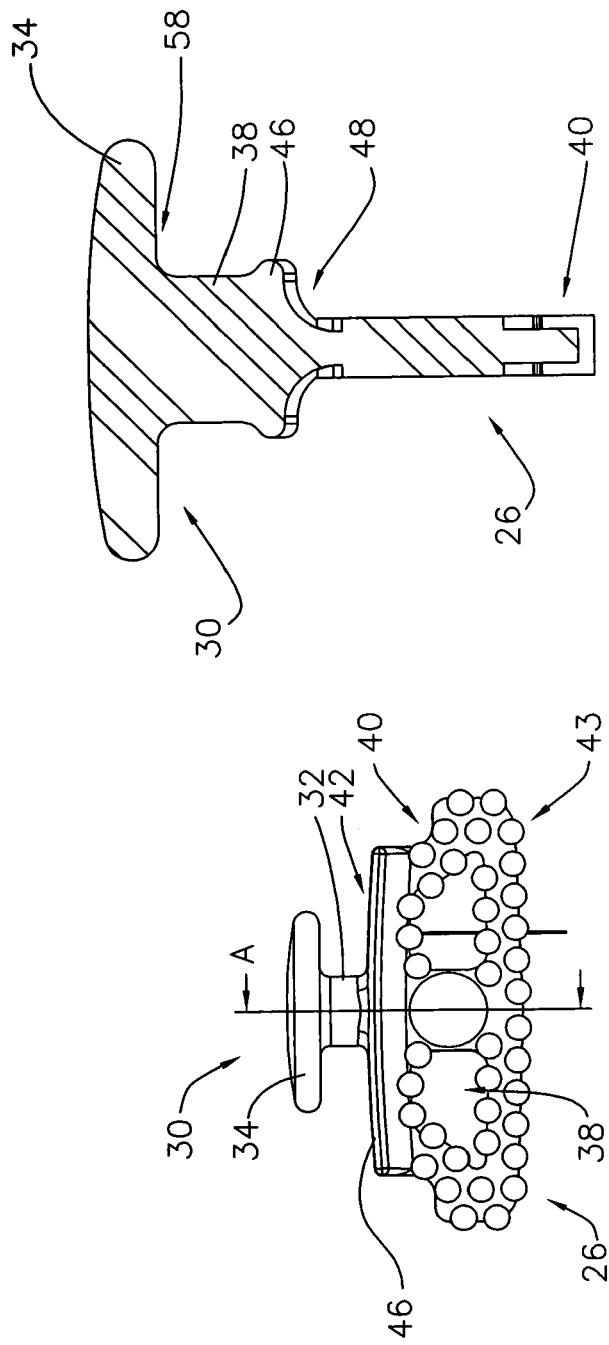
FIG. 3
FIG. 5
FIG. 2
FIG. 4

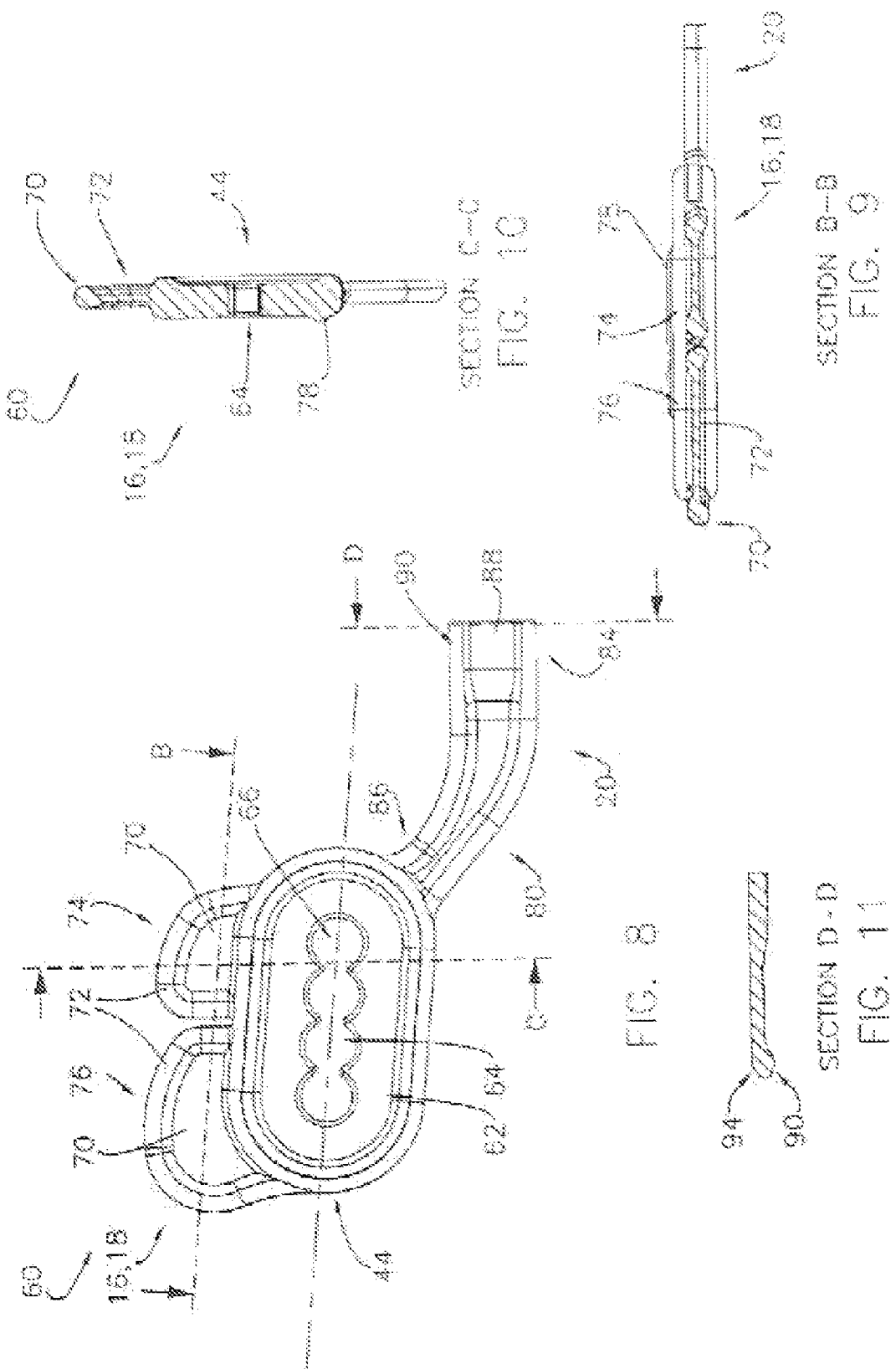

DENTAL APPLIANCE FOR MINIMIZING EFFECTS OF BRUXISM

BACKGROUND OF THE INVENTION

1. Filed of the Invention

The present invention relates generally to dental appliances for protecting the occlusal area of the mouth from the effects of bruxism. More specifically, the present invention concerns a dental appliance for maintaining a separation or space between the occlusal plane surfaces of the rear or posterior teeth in order to avoid or minimize the adverse effects of bruxism, especially while sleeping.

2. Description of the Prior Art

Bruxism can occur under a variety of circumstances, including involuntarily while sleeping. Adverse physiological effects of bruxism include worn, broken, loose, or sensitive teeth; receding gums; periodontal pockets; bony ridges (tori); cheek irritation; sore musculature, especially in the cheek and temple area; headaches; and problems of the temporomandibular joint, such as pain or soreness.

Dental appliances are known in the prior art to be worn during sleeping for minimizing these and other adverse effects. Some such prior art appliances are very expensive and therefore less accessible to suffers of bruxism. Other such prior art devices are more affordable, such as, for example, those disclosed in U.S. Pat. Nos. 5,873,365 and 6,152,138. Of course, these appliances can only work if they are used regularly and properly by suffers of bruxism, and such sufferers are less likely to use an appliance that is uncomfortable to wear or cumbersome to maintain. Thus, though the aforementioned prior art appliances will function to reduce the effects of bruxism when worn, improvements in comfort and durability are needed.

SUMMARY OF THE INVENTION

The present invention overcomes the above-described problems and other limitations in the prior art by providing a dental appliance for maintaining a separation or spacing between the occlusal plane surfaces of the rear or posterior teeth in order to avoid or minimize the adverse effects of bruxism, especially while sleeping. The appliance broadly comprises left and right bitepad assemblies and left and right side assemblies connected by a strap assembly.

The left and right bitepad assemblies are each adapted and operable to fit between the rear or posterior teeth and maintain the aforementioned separation or spacing thereof. Each bitepad assembly broadly includes a bitepad having a core substantially covered by an overmold, and a pin subassembly having a shank projecting from an outer side surface of the bitepad and terminating in a disk or other capping feature. The core provides a structural component for supporting the overmold, and is preferably constructed of a harder material than the overmold. Large openings are provided in an interior area of the core to create mechanical locks and increase the molecular bond between the core and the overmold, and large corner voids or notches on opposite end surfaces of the core provide additional mechanical locks to further increase durability and adhesion. Additionally, three-dimensional solid projections are provided through, from, or on the core to provide substantially greater surface area for the overmold to bond to, thereby further enhancing adhesion and durability. The overmold is molded or otherwise applied over the core to provide a more comfortable contact surface, and is preferably constructed of a softer material than the core.

An optional extension or stabilizer may be provided projecting from the bitepad perpendicular to the bite surface to fit into and engage the interproximal area between two teeth. The stabilizer thereby further facilitates retention of the bitepad in its proper operating position.

The left and right side assemblies are each adapted and operable to receive and securely retain respective bitepad assemblies in their proper operating positions. Each side assembly broadly includes a receiver and a projecting flange or wing. The flanges project from an upper surface of the receiver. The flanges reside, in use, along the upper gum tissue and help to stabilize the appliance in the mouth, including while talking or performing other activities involving opening the mouth. Each flange is separated into two distinct front and rear portions, each of which is able to flex independently of the other and thereby better accommodate the gum and jaw profiles, particularly the zygomatic arch. The flanges are also offset outwardly from the longitudinal centerline of the receiver, thereby better accommodating the shallowing contour of the gum line vestibule in the maxilla and mandible. An elongated bumper or similar projection may be provided on a lower inner surface of the receiver to better accommodate the overlap of the upper teeth relative to the bottom teeth in what is called "occlusal coupling".

The strap assembly physically connects the left and right side assemblies and assists in retaining the side assemblies and the bitepad assemblies associated therewith in proper operating position. The strap assembly broadly includes left and right lateral connector sections and a center bridge section. The lateral connectors physically connect the bridge with the side assemblies. The mesial area of the bridge is made thicker and therefore more rigid which causes the strap assembly to flare around protruding gum tissue at the intersections of the bridge and the lateral connectors in the root area of the cuspid teeth. Furthermore, an offset parting line allows for a larger radius on the inner side of the strap assembly which contacts the gum tissue, thereby further avoiding pressure points and enhancing comfort.

Thus, it will be appreciated that the appliance of the present invention provides a number of advantages over the prior art, including, for example, that the solid projections and mechanical locks of the core of the bitepad advantageously provide significantly enhanced bonding with the overmold and thereby enhance durability. Furthermore, the divided flange or wing advantageously results in independent flexibility and better conformity and thereby enhances stability and comfort. Additionally, the thickened mesial area of the bridge advantageously results in a flare in the area of the cuspid roots and thereby avoids or minimizes irritation and discomfort to the gum tissue in that area.

These and other important features of the present invention are more fully described in the section titled DETAILED DESCRIPTION OF A PREFERRED EMBODIMENT, below.

BRIEF DESCRIPTION OF THE DRAWINGS

A preferred embodiment of the present invention is described in detail below with reference to the attached drawing figures, wherein:

FIG. 2 is a plan view of a core and pin subassembly of a bitepad assembly of the dental appliance shown in FIG. 1;

FIG. 3 is a section view through line AA of the core and pin subassembly shown in FIG. 2;

FIG. 4 is a plan view of an overmold component of the dental appliance shown in FIG. 1;

FIG. 5 is an elevation view of the overmold component shown in FIG. 4;

FIG. 6 is a front view of the overmold component shown in FIG. 4;

FIG. 7 is a front view of the bitepad assembly shown with an optional stabilizer component;

FIG. 8 is a fragmentary view of a side assembly component of the dental appliance shown in FIG. 1;

FIG. 9 is a section view through line BB of the flange portion of the side assembly shown in FIG. 8; and FIG. 10 is a section view through line CC of a receiver portion and flange portion of the side assembly shown in FIG. 8;

FIG. 11 is a section view through line DD of the strap assembly component of the dental appliance shown in FIG. 8.

DETAILED DESCRIPTION OF THE PREFERRED EMBODIMENTS

Figure 1:
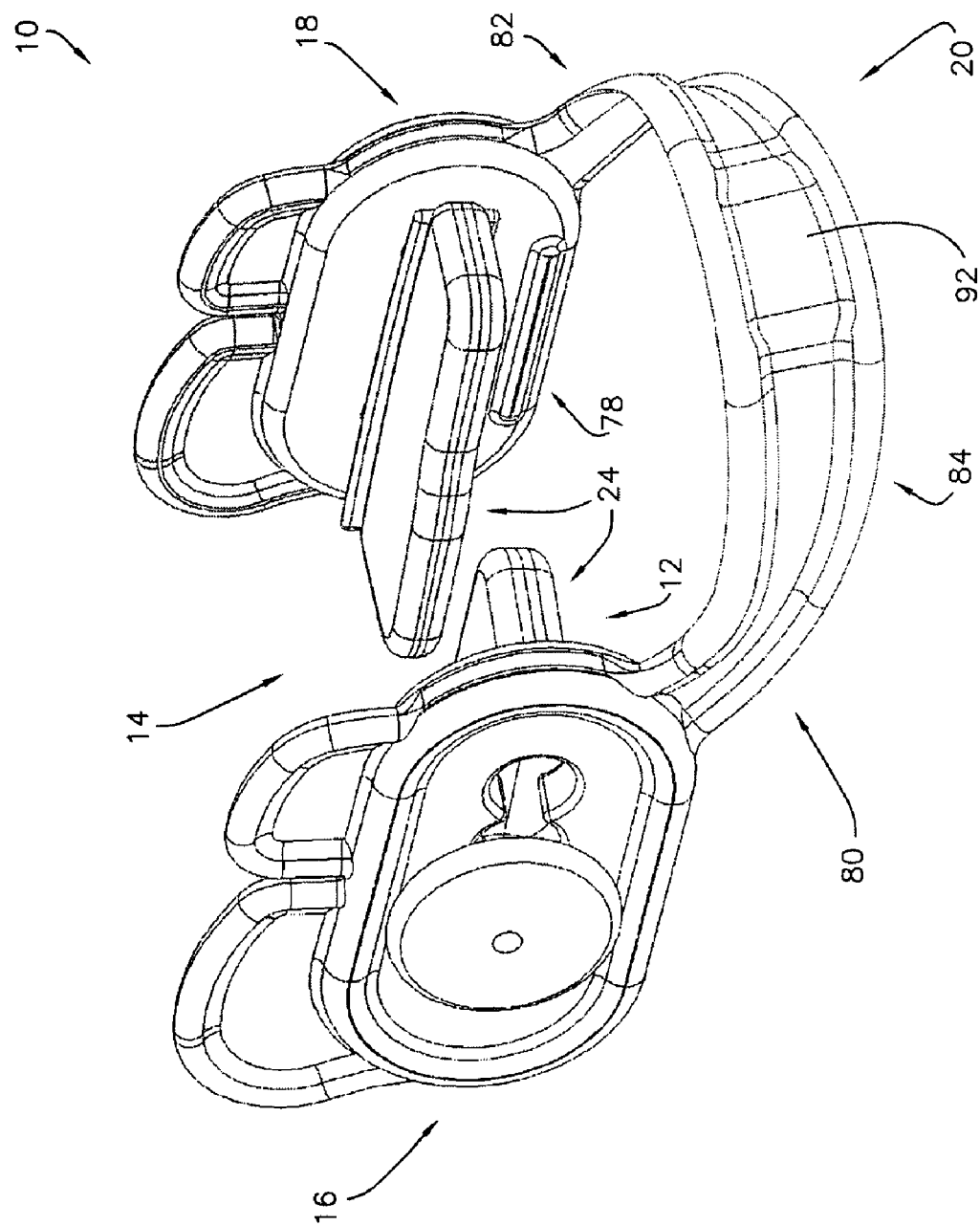
FIG. 1 is an isometric view of a preferred embodiment of the dental appliance of the present invention.

With reference to the figures, a dental appliance 10 is herein described shown, and otherwise disclosed in accordance with the preferred embodiment of the present invention. Broadly, the appliance 10 maintains a separation or spacing between the occlusal plane surfaces of the rear or posterior teeth (i.e., molars and pre-molars) in order to avoid or minimize the adverse effects of bruxism (i.e., teeth clenching or grinding), especially while sleeping. The appliance includes substantial improvements over prior art designs, which have the advantageous and desirable effects of increasing user compliance through enhanced comfort and durability. Representative prior art appliances are described, for example, in U.S. Pat. Nos. 5,873,365 and 6,152,138, the disclosures of which are hereby incorporated by reference into the present application.

Referring to FIG. 1, the appliance 10 broadly comprises left and right bitepad assemblies 12,14 and left and right side assemblies 16,18 connected by a strap assembly 20. These components may be constructed from one or more resilient polymeric or similarly suitable materials. Furthermore, the components may be manufactured using any suitable technique or combinations of techniques such as, for example, stamping, injection molding, or vacuum forming.

Bitepad Assemblies

Referring also to FIGS. 2-6, the left and right bitepad assemblies 12,14 are each adapted and operable to fit between the rear or posterior teeth and maintain the aforementioned separation or spacing thereof. Each bitepad assembly 12,14 broadly includes a bitepad 24 having a core 26 substantially covered by an overmold 28, and a pin subassembly 30 having a shank 32 projecting from an outer side surface of the bitepad 24 and terminating in a disk or other capping feature 34.

With the jaw in a resting position, a natural space exists between the upper and lower posterior teeth (i.e., all teeth distal of the cuspids). During grinding, these teeth are subject to approximately 80% of the applied force. The bitepad 24 has an overall thickness approximately equal to this natural space, and, in use of the appliance 10, is positioned and retained therein, in physical contact with the posterior teeth, in order to preserve the natural spacing and thereby maintain a desired separation between these teeth.

The bitepad 24 is shaped to better accommodate the natural shape of the teeth and jaw. More specifically, the occlusion between the upper and lower teeth forms a first natural curve, called the "Curve of Spee", in the mesial-distal directions, and a second natural curve, called the "Curve of Wilson" in the buccal directions (i.e., perpendicular to the first natural curve). Thus, the bitepad, particularly the upper and lower surfaces thereof, is appropriately shaped to accommodate these curves (best seen in FIGS. 5 and 6), thereby enhancing comfort and wearability. Furthermore, the mesial end of the bitepad 24, which contacts the pre-molars, is narrower than the distal end (best seen in FIG. 4), which contacts the molars and wisdom teeth, in order to better accommodate the teeth while maximizing comfort.

The core 26 provides a structural component for supporting the overmold 28, and is preferably constructed of a harder material than the overmold 28. The thickness of the core is preferably sufficiently thick to avoid structural weakness and sufficiently thin to avoid adversely affecting the design of the overmold 28. More specifically, a thicker core would require a thinner overmold in order to achieve, within a reasonable range, the desired overall thickness of the bitepad.

Large openings 38 are provided in an interior area of the core 26 to create mechanical locks and increase the molecular bond between the core 26 and the overmold 28. Large corner voids or notches 40 on opposite end surfaces of the core 26 provide additional mechanical locks to further increase durability and adhesion.

Three-dimensional solid projections 43 are provided through, from, or on the core 26 to provide substantially greater surface area for the overmold 28 to bond to, thereby further enhancing adhesion and durability. In one implementation, these projections 43 increased total surface area by approximately 25%, or between approximately 10% and 40%. Though shown as being substantially cylindrical, the projections may be of substantially any desired shape, including, for example, pyramidal, cubal, spherical, or irregular.

The core's out side 42 which is, in use, closest to a receiver portion 44 of the side assembly 16,18 (see FIG. 8), is provided with a slight concave arc to allow for easier articulation of the pin subassembly 30 within the receiver 44, thereby making repositioning of the bitepad 24 easier. A raised rib 46 is provided along this surface of sufficient height to reduce the risk of undesired removal of the bitepad assembly 12,14 from the receiver 44 in the buccal direction. Large radii 48 at the intersection of the rib 46 and the core 26 are provided to enhance the security and durability of the connection.

The overmold 28 is molded or otherwise applied over the core 26 to provide a more comfortable contact surface, and is preferably constructed of a softer material than the core 26. Furthermore, these materials are preferably molecularly similar such that, when the overmold is introduced to the core under heat and pressure, they bond together and thereby further assist in coupling the overmold with the core. For example, the core 26 and overmold 28 may both be constructed of polyurethane or polypropylene material with different additives added to make the material harder, in the case of the core 26, or softer, in the case of the overmold 28. Large radii 50 on the inward surfaces of the overmold 28 are provided to improve comfort in the lingual area of the mouth.

The aforementioned improvements for increasing durability of and adhesion between the overmold 28 and the core 26 result in the present invention being better able than the prior art to endure the approximately 250 lbs/in$^2$ of force that can be generated by grinding teeth.

Referring also FIG. 7, an optional extension or stabilizer 54 may be provided projecting from the bitepad 24 perpendicular to the bite surface to fit into and engage the interproximal area between two teeth. The stabilizer 54 thereby further facilitates retention of the bitepad 24 in its proper operating position.

The pin subassembly 30 is received and retained in the receiver 44 of the side assembly 16,18 by the disk or cap 34 on the outward side and the rib 46 on the inward side and the shaft 32 extending therebetween and through the receiver 44. This retention mechanism allows the bitepad 24 to tilt and assume an angular orientation which is particular to the individual user's occlusal surfaces. Thus, the bitepad 24 is both rotatably and longitudinally adjustable in relation to the side assembly 16,18.

The shaft preferably has a diameter which is large enough to provide sufficient strength to avoid breakage under the aforementioned chewing pressure, but which is also small enough to avoid requiring an opening in the receiver 44 so large that retention of the bitepad assembly 12,14 is jeopardized. A radius 58 at the intersection of the cap 34 and shaft 32 is preferred to aid in retention of the bitepad assembly 12,14 during chewing. Similarly, the disk or cap 34 is preferably large enough to retain the bitepad assembly 12,14 in the receiver 44 by avoiding undesired removal in the mesial direction, but also small enough to allow the receiver 44 to be of a reasonable size.

Side Assemblies

Referring also to FIGS. 8-11, the left and right side assemblies 16,18 are each adapted and operable to receive and securely retain respective bitepad assemblies 12,14 in their proper operating positions. Each side assembly 16,18 broadly includes the earlier-mentioned receiver 44 and a projecting flange or wing 60.

The receiver 44 presents inward and outward surfaces. The outward surface includes an elongated channel 62. One or more distinct holes, a single elongated hole, or, as shown, one or more overlapping holes 64 are provided in a central region of the channel 62, extending completely through the receiver 44 from the inward to the outward sides. The shaft 32 of the pin subassembly 30 of the bitepad assembly 16,18 passes though one of these holes 64, with the disk or cap 34 being received within the elongated channel 62 to further improve comfort.

The overlapping holes 64 are radiused to provide smoother movement of the shaft 34 from one hole to another. Furthermore, the receiver 44, or, at least, the elongated channel 62 and holes 64 therein, is provided with an angle or arc (shown by reference to a centerline 66) such that movement of the bitepad assembly 12,14 backward or forward in the receiver 44 to accommodate respectively larger or smaller mouths. This adjustability of the bitepad assemblies 12,14 relative to the side assemblies 16,18 enables the appliance 10 to accommodate the different dental structures of different wearers. The rearmost holes of the plurality of overlapping holes 64 may be utilized by wearers with larger bites, whereas the foremost holes may be utilized by wearers with smaller bites.

The flanges 60 project upwardly from an upper surface of the receiver 44. The flanges 60 reside, in use, along the upper gum tissue and help to stabilize the appliance 10 in the mouth, including while talking or performing other activities involving opening the mouth. As best seen in FIG. 10, the flanges 60 are offset outwardly from the longitudinal centerline of the receiver 44, thereby better accommodating the shallowing contour of the gum line vestibule in the maxilla and mandible. Each flange 60 presents an interior portion 70 at least partially surrounded by a thicker rounded lip portion 72. The interior portion 70 is preferably made as thin as possible in order to achieve the highest flexural modulus while maintaining sufficient structural integrity. The lip 72, however, is thicker than the interior portion 70 and rounded to protect the gum tissue and otherwise enhance comfort. It is contemplated that the interior portion 70 may, on the inner surface which contacts the gum tissues, interface flushly with the lip 72, such that the inner surface is substantially flat, thereby further enhancing comfort. It is also contemplated that the interior area 70 may be a void defined only by the surrounding lip 72, thereby further increasing overall flexibility of the flange 60.

Each flange 60 is separated into multiple substantially distinct portions, including front and rear portions 74,76. Each portion 74,76 is able to flex independently of the other and thereby better accommodate the gum and jaw profiles, particularly the zygomatic arch. It will be appreciated that the flange 60 may be separated or divided into any practical number of such substantially distinct portions to further improve flexibility and ability to conform to the particular user.

In the mouth, the upper teeth overlap the bottom teeth in what is called "occlusal coupling". To better accommodate this uneven surface, an elongated bumper or similar projection 78 is provided on a lower portion of the inner surface of the receiver 44.

Strap Assembly

The strap assembly 20 physically connects the left and right side assemblies 16,18 and assists in retaining the side assemblies 16,18 and the bitepad assemblies 12,14 associated therewith in proper operating position. The strap assembly 20 is preferably constructed of a material that is soft, has a high flex modulus, and shapes or conforms at body temperature to achieve a desired level of comfort, and, furthermore may have an amount of memory to facilitate retaining this desired shape. One suitable material is, for example, a resin with a very high component or percentage of vinyl acetate. The strap assembly 20 broadly includes left and right lateral connector sections 80,82 and a center bridge section 84.

The lateral connectors 80,82 physically connect the bridge 84 with the side assemblies 16,18. The bridge 84 is located, in use, substantially lower in the mouth than the side assemblies 16,18. More specifically, whereas the side assemblies 16,18 are at the level of the teeth and associated with the natural space between the upper and lower posterior teeth, the bridge 84 is located along and rests against the gum tissue covering the roots of the lower anterior teeth. This configuration advantageously minimizes interference from wearing the appliance 10 with such activities as talking, eating, and breathing. Small abrupt radii 86 are provided at the intersection of the lateral connectors 80,82 and the receiver 44 to allow these areas to flex and torque independently.

The strap assembly 20 preferably has a height which is sufficiently large to adequately disperse pressures across maximum gum tissue surface area and thereby causing less friction and discomfort, but also sufficiently small to avoid being cumbersome to wear. The strap assembly 20 has a substantially flat and relatively thin interior portion 88 between thicker rounded upper and lower lip portions 90. The thinner interior portion 88 allows for greater flexibility while keeping the strap assembly 20 wide and flat against the gum tissue to enhance comfort. The mesial area 92 of the forward portion of the bridge 84 is, however, made thicker and therefore more rigid which causes the strap assembly 20 to flare around protruding gum tissue at the intersections of the bridge 84 and the lateral connectors 80,82 in the root area of the cuspid teeth.

As best seen in FIG. 11, an offset parting line allows for a larger radius 94 on the inner side of the upper and lower lip portions 90 that contact the gum tissue, thereby further avoiding pressure points and enhancing comfort.

From the preceding description, it will be appreciated that the appliance of the present invention provides a number of advantages over the prior art, including, for example, that the solid projections and mechanical locks of the core of the bitepad advantageously provide significantly enhanced bonding with the overmold and thereby enhance durability. Furthermore, the divided flange or wing advantageously results in independent flexibility and better conformity and thereby enhances stability and comfort. Additionally, the thickened mesial area of the bridge advantageously results in a flare in the area of the cuspid roots and thereby avoids or minimizes irritation and discomfort to the gum tissue in that area.

Although the invention has been described with reference to the preferred embodiments illustrated in the drawings, it is noted that equivalents may be employed and substitutions made herein without departing from the scope of the invention as recited in the claims.

Having thus described the preferred embodiment of the invention, what is claimed as new and desired to be protected by Letters Patent includes the following:

What is claimed is:

1. A dental appliance comprising:
   a pair of bitepad assemblies for maintaining a separation between upper and lower teeth, with each bitepad assembly including a bitepad having
      a core presenting a plurality of solid projections,
      an overmold substantially covering the core, wherein the plurality of solid projections assist in coupling the overmold with the core,
      wherein the core is constructed of a harder material for durability, and the overmold is constructed of a softer material for comfort, and
      one or more openings created in the core to act as mechanical locks and thereby assist in coupling the overmold with the core;
   a pair of side assemblies, with each side assembly being adapted to retain a respective one of the bitepad assemblies in a proper operating position; and
   a strap assembly for connecting the pair of side assemblies.

2. The dental appliance as set forth in claim 1, wherein the core and the overmold are constructed of molecularly similar materials that, when the overmold is introduced to the core under heat and pressure, bond together and thereby assist in coupling the overmold with the core.

3. The dental appliance as set forth in claim 1, wherein the plurality of solid projections are cylindrical and project from one or more surfaces of the core.

4. A dental appliance comprising:
   a pair of bitepad assemblies, with each bitepad assembly including a bitepad for maintaining a separation between upper and lower teeth;
   a pair of side assemblies, with each side assembly being adapted to retain a respective one of the bitepad assemblies in a proper operating position, and each side assembly including
      a receiver for adjustably retaining the bitepad, the receiver including a plurality of selectable forward and rearward positions for retaining the bitepad, and wherein the plurality of selectable forward and rearward positions are arranged substantially on a line that deviates from horizontal such that the selectable forward positions are lower than the selectable rearward positions, and
      a flange projecting from the receiver so as to be positioned, during use, substantially against gum tissue associated with the teeth, and including a first flange portion and a second flange portion which are substantially independently flexible; and
   a strap assembly for connecting the pair of side assemblies.

5. The dental appliance as set forth in claim 4, wherein the receiver includes an elongated channel in which the plurality of selectable forward and rearward positions are located, and wherein the bitepad assembly presents both a shaft that extends through the receiver and a shape at the end of the shaft to assist in retaining the bitepad to the receiver, and wherein the shape at the end of the shaft resides substantially within the channel.

6. The dental appliance as set forth in claim 4, wherein the flange projects from the receiver at a location that is offset outwardly from a midline of the receiver.

7. A dental appliance comprising:
   a pair of bitepad assemblies for maintaining a separation between upper and lower teeth;
   a pair of side assemblies, with each side assembly being adapted to retain a respective one of the bitepad assemblies in a proper operating position; and
   a strap assembly for connecting the pair of side assemblies, with the strap assembly including
      a pair of lateral connectors, with each lateral connector being connected at one end to a respective one of the side assemblies, and
      a bridge connecting the pair of lateral connectors, with the bridge being flared near the lateral connectors to accommodate an area of projecting gum tissue, wherein the flaring of the bridge is accomplished by thickening a mesial area of the bridge.

8. The dental appliance as set forth in claim 7, wherein the bridge is positioned along gum tissue covering roots of lower anterior teeth, and the flaring of the bridge accommodates projecting roots of cuspid teeth.

9. A dental appliance for minimizing effects of bruxism, the dental appliance comprising:
   a pair of bitepad assemblies for maintaining a separation between upper and lower teeth, with each bitepad assembly including a bitepad having
      a core presenting a plurality of solid projections,
      an overmold substantially covering the core, wherein the plurality of solid projections assist in coupling the overmold with the core,
      wherein the core is constructed of a harder material for durability, and the overmold is constructed of a softer material for comfort, and
      wherein the core and the overmold are constructed of molecularly similar materials that, when the overmold is introduced to the core under heat and pressure, bond together and thereby assist in coupling the overmold with the core;
   a pair of side assemblies, with each side assembly being adapted to retain a respective one of the bitepad assemblies in a proper operating position, and each side assembly including
      a receiver for adjustably retaining the bitepad, and a flange projecting from the receiver so as to be positioned, during use, substantially against gum tissue associated with the teeth, and including a first flange portion and a second flange portion which are substantially independently flexible; and
   a strap assembly for connecting the pair of side assemblies, the strap assembly including a pair of lateral connectors, with each lateral connector being connected at one end to a respective one of the side assemblies, and a bridge connecting the pair of lateral connectors, with the bridge having a thickened mesial area to cause a flaring effect to accommodate an area of projecting tissue.

10. The dental appliance as set forth in claim 9, wherein the plurality of solid projections are cylindrical and project from one or more surfaces of the core.

11. The dental appliance as set forth in claim 9, wherein the receiver provides a plurality of selectable forward and rearward positions for retaining the bitepad, and wherein the plurality of selectable forward and rearward positions are ananged substantially on a line that deviates from horizontal such that the selectable forward positions are lower than the selectable rearward positions.

12. The dental appliance as set forth in claim 11, wherein the receiver includes an elongated channel in which the plurality of selectable forward and rearward positions are located, and wherein the bitepad assembly presents both a shaft that extends through the receiver and a shape at the end of the shaft to assist in retaining the bitepad to the receiver, and wherein the shape at the end of the shaft resides substantially within the channel.

13. The dental appliance as set forth in claim 9, wherein the flange projects from the receiver at a location that is offset outwardly from a midline of the receiver.

14. The dental appliance as set forth in claim 9, wherein the bridge is positioned along gum tissue covering roots of lower anterior teeth, and the flaring effect accommodates projecting roots of cuspid teeth.

15. A dental appliance for minimizing effects of bruxism, the dental appliance comprising:

a pair of bitepad assemblies for maintaining a separation between upper and lower teeth, with each bitepad assembly including a bitepad having a core presenting a plurality of solid projections, an overmold substantially covering the core, wherein the plurality of solid projections assist in coupling the overmold with the core, wherein the core is constructed of a harder material for durability, and the overmold is constructed of a softer material for comfort, and one or more openings created in the core to act as mechanical locks and thereby assist in coupling the overmold with the core;

a pair of side assemblies, with each side assembly being adapted to retain a respective one of the bitepad assemblies in a proper operating position, and each side assembly including a receiver for adjustably retaining the bitepad, and a flange projecting from the receiver so as to be positioned, during use, substantially against gum tissue associated with the teeth, and including a first flange portion and a second flange portion which are substantially independently flexible; and a strap assembly for connecting the pair of side assemblies, the strap assembly including a pair of lateral connectors, with each lateral connector being connected at one end to a respective one of the side assemblies, and a bridge connecting the pair of lateral connectors, with the bridge having a thickened mesial area to cause a flaring effect to accommodate an area of projecting tissue.

* * * * *